US007891357B2

(12) United States Patent
Carron et al.

(10) Patent No.: US 7,891,357 B2
(45) Date of Patent: Feb. 22, 2011

(54) BREATHING APPARATUS, PARTICULARLY OF THE OPEN-CIRCUIT TYPE

(75) Inventors: Gerard Carron, Saint Alban de Roche (FR); Franck Laurent, Saint Alban de Roche (FR)

(73) Assignee: Materiels Industriels de Securite (FR)

( * ) Notice: Subject to any disclaimer, the term of this patent is extended or adjusted under 35 U.S.C. 154(b) by 727 days.

(21) Appl. No.: 11/873,481

(22) Filed: Oct. 17, 2007

(65) Prior Publication Data

US 2008/0173307 A1 Jul. 24, 2008

(30) Foreign Application Priority Data

Oct. 17, 2006 (FR) .................................. 06-09073

(51) Int. Cl.
*A61M 11/00* (2006.01)

(52) U.S. Cl. ............................ 128/205.22; 128/200.24

(58) Field of Classification Search ............ 128/205.22, 128/205.24, 200.24, 201.27, 201.28, 204.26, 128/204.18

See application file for complete search history.

(56) References Cited

U.S. PATENT DOCUMENTS 4,062,356 A * 12/1977 Merrifield ............. 128/205.22
4,722,333 A * 2/1988 Bartos ................... 128/202.27
6,290,111 B1 * 9/2001 Hedenberg et al. .......... 224/262
6,973,928 B1 * 12/2005 Taylor et al. ........... 128/200.24
7,066,172 B2 * 6/2006 Pasternack ............. 128/202.22
7,380,551 B2 * 6/2008 Alvey .................... 128/201.25
7,748,380 B1 * 7/2010 Phifer et al. ........... 128/201.25
2003/0116156 A1 * 6/2003 Jackson ................. 128/201.22
2006/0048777 A1 * 3/2006 Brookman ............. 128/201.22

* cited by examiner

*Primary Examiner*—Steven O Douglas
(74) *Attorney, Agent, or Firm*—Cantor Colburn LLP

(57) ABSTRACT

The invention relates to breathing apparatus, particularly of the open-circuit type, comprising a backpiece equipped with means, particularly involving straps, to allow it to be worn on the back of a wearer, the backpiece being intended to support at least one cylinder equipped with a valve, the backpiece being equipped with a coupling which, intended to collaborate with the valve, is connected to a regulator. The coupling comprises an air intake tube on which a bushing is mounted such that it can pivot and move in terms of axial translation. The bushing is mounted in a sleeve that forms an operating knob, is prevented from turning in the sleeve and is free in terms of translational movement with respect to the latter.

10 Claims, 6 Drawing Sheets

BREATHING APPARATUS, PARTICULARLY OF THE OPEN-CIRCUIT TYPE

TECHNICAL FIELD OF THE INVENTION

The invention relates to breathing apparatus, particularly of the open-circuit type.

BRIEF DESCRIPTION OF RELATED ART

Apparatus such as this is used to afford respiratory protection and to allow individuals to move around in a toxic or asphyxiating atmosphere, both in the field of industry and in the field of emergency response.

Apparatus such as this generally comprises a backpiece equipped with means, particularly involving straps, to allow it to be worn on the back of a wearer, the backpiece being intended to support at least one cylinder equipped with a valve comprising a tapped internal housing, the backpiece being equipped with a coupling which, intended to collaborate with the valve, is connected to a regulator.

The coupling usually consists of a simple screw forming an air intake tube and connected to the regulator.

Breathing apparatus such as this has a limited period of use which is dependent on the volume and pressure of the cylinder that forms the air supply. It is thus necessary to be able to change the cylinder easily, particularly when operating in a hostile environment.

Conventional breathing apparatus, in order to do this, has to be taken off the wearer, the cylinder having to be changed in a horizontal position owing to the need, when screwing, to maintain the position of the tapped housing of the valve with respect to the coupling formed by the screw.

Taking the apparatus off is detrimental because it greatly lengthens the time taken to change the cylinder. What is more, the combined operations of turning the screw and keeping the cylinder in position are tricky.

BRIEF SUMMARY OF THE INVENTION

The invention allows the cylinder to be changed quickly and easily, while still on the wearer's back, that is to say without needing the apparatus to be taken off.

To this end, the invention relates to breathing apparatus of the aforementioned type, wherein the coupling comprises an air intake tube, protruding outward, on which a bushing is mounted such that it can pivot and move in terms of axial translation, the bushing comprising an externally threaded first region situated toward the free end of the tube and intended to collaborate with the tapped housing of the valve of the cylinder, and a second region intended to be mounted in a sleeve that forms an operating knob, the screw-forming bushing being prevented from turning in the sleeve and free in terms of translational movement with respect to the latter, the sleeve being mounted such that it can pivot on the coupling about the axis of the tube and prevented from translational movement with respect to this tube.

Thus, upon coupling, the housing of the valve fits onto the free end of the tube, thus centering the valve with respect to the screw-forming bushing, the valve pushing the latter toward the backpiece.

When the operator turns the sleeve he is able then to screw the bushing into the tapped housing of the valve, so as to make the connection.

This then yields a coupling which is simple to use because the operations of positioning the valve with respect to the coupling and of turning the screw are separated, the tube being able to provide support prior to screwing.

Advantageously, the free end of the tube comprises a region of a diameter substantially equal to the diameter of the housing of the valve.

This then guarantees that the valve is accurately centered with respect to the tube, and, therefore, that the tapped thread in the housing of the valve is precisely centered with respect to the screw thread on the bushing.

According to one feature of the invention, the length of the tube is at least equal to the depth of the housing increased by the length of the screw-forming bushing.

This arrangement allows the screw to be withdrawn sufficiently when the valve is being positioned on the free end of the tube.

As a preference, an elastic element, particularly a helical compression spring, is mounted between the regulator or the sleeve and the bushing.

The elastic element thus forces the bushing, and more specifically the threaded region thereof, against the tapped thread of the valve, so that they can start being screwed together when the sleeve and the bushing are turned.

According to one embodiment of the invention, the length of the sleeve is at least equal to the length of the bushing.

The end of the sleeve thus protrudes beyond the bushing as the valve is inserted, which means that the sleeve can also contribute to guiding the valve.

Advantageously, the bushing is equipped with a coupling rod, for example, a screw, extending radially outward, the rod fitting into an oblong slot formed in the sleeve.

A coupling such as this is simple to achieve and allows the bushing and the sleeve to be connected in terms of rotation while at the same time allowing the bushing some translational movement relative to the sleeve.

As a preference, the bushing is equipped with identification elements projecting into the oblong slot.

The identification elements thus visible from the outside to the operator who is screwing the cylinder on to the valve provide a better visual appreciation of the position of the bushing, and therefore allow the operator to make sure that he is screwing the components together correctly.

According to one feature of the invention, the breathing apparatus comprises a cover, fixed to the backpiece and at least partially covering the latter together with the regulator.

Advantageously, the breathing apparatus comprises a cylinder support having at least three points of contact positioned in such a way as to define a V directed at right angles to the plane of the backpiece, and which are intended to support a cylinder.

The V-shaped support allows the cylinder to be held firmly in position irrespective of its diameter.

As a preference, the support comprises two additional lateral points of contact, each one intended to support a cylinder.

The additional points of contact mean that two cylinders can easily be positioned on one and the same backpiece.

BRIEF DESCRIPTION OF THE DRAWINGS

In any event, the invention will be clearly understood with the aid of the description which follows, with reference to the attached schematic drawing, which, by way of nonlimiting example, depicts one embodiment of this breathing apparatus.

DETAILED DESCRIPTION OF THE INVENTION

Figure 1:
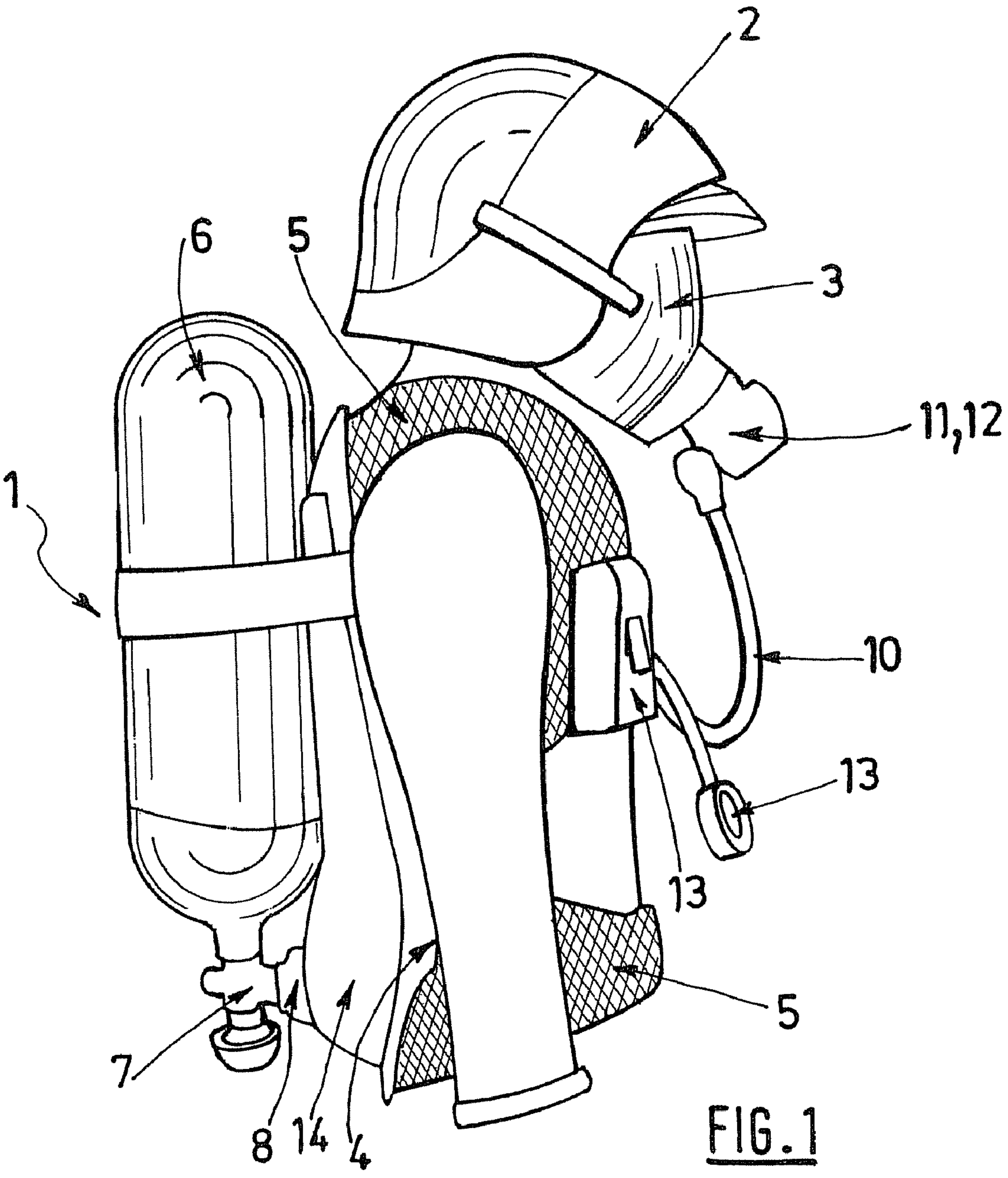
FIG. 1 is a side view of breathing apparatus according to the invention, in position on the wearer.

FIG. 1 depicts breathing apparatus 1 according to the invention, of the open-circuit type, in position on the back of a wearer.

The wearer is equipped with a helmet 2 to which there is attached an airtight mask 3 which covers the face, and particularly the airways, of the wearer.

The latter is also equipped with breathing apparatus 1 comprising a backpiece 4 equipped with straps 5 that fit over his shoulders and around his waist.

Figure 4:
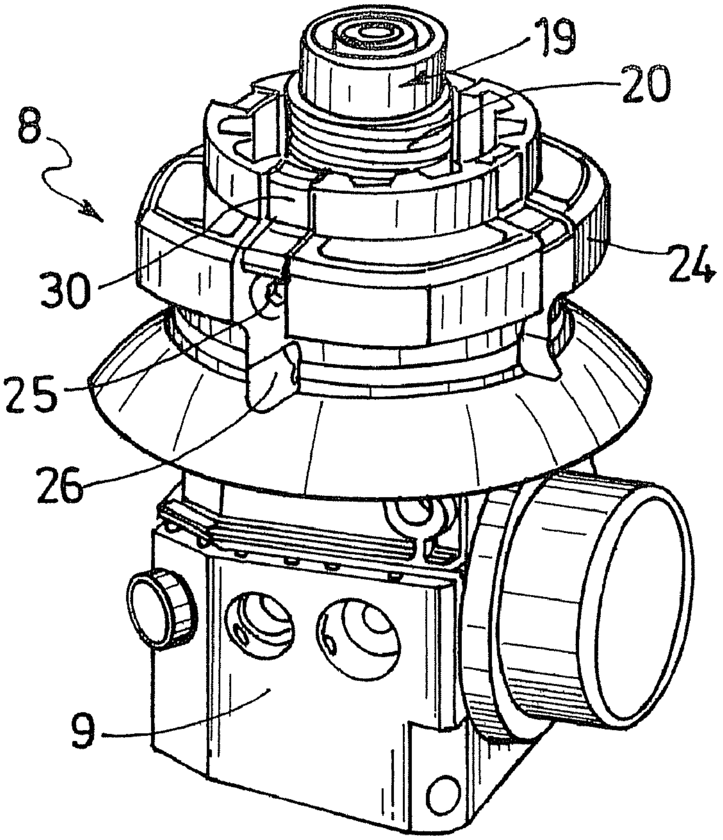
FIG. 4 is an enlarged perspective view of a regulator equipped with a coupling.
Figure 5:
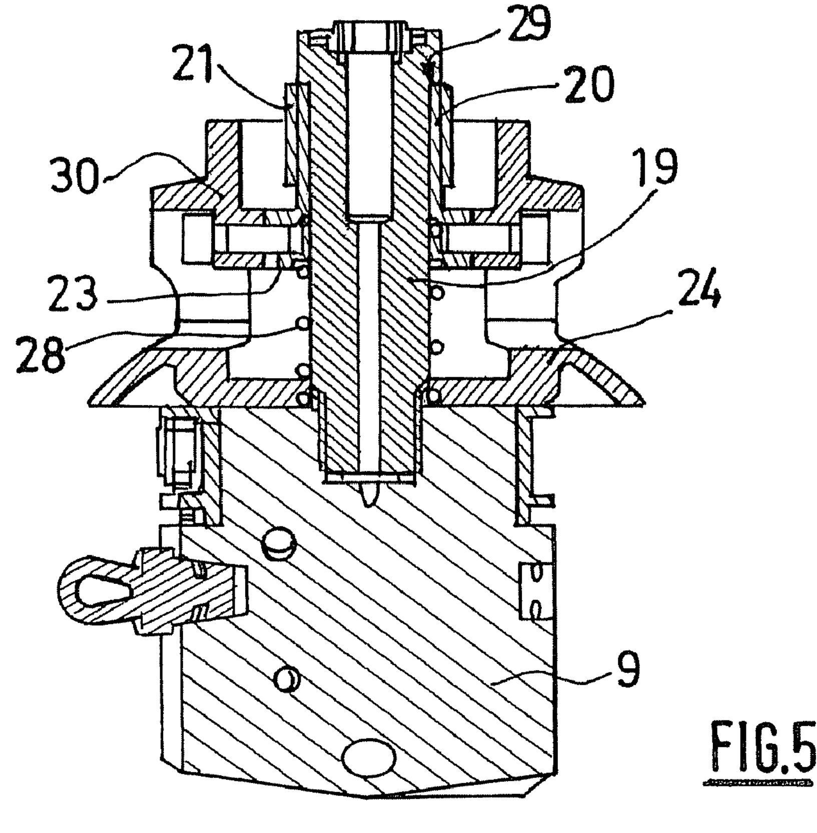
FIG. 5 is a view in longitudinal section of the coupling and of the regulator.

The backpiece supports a cylinder 6 that forms a supply of compressed air, equipped with a valve 7 comprising a tapped internal housing, as is known per se, the valve collaborating with a coupling 8 which, mounted on the backpiece 4, is connected to a regulator, visible under the reference 9 in FIG. 4 particularly.

The regulator 9 mounted on the backpiece 4, also known as a high-pressure regulator, reduces the pressure of the compressed air stored between 200 and 300 bar (1 bar=101 300 Pa) in the cylinder 6, down to a pressure of about 7 bar.

A flexible tube 10 carries the air from this high-pressure regulator 9 to a second regulator 11, known as a low-pressure regulator, attached to the wearer's mask 3 and reducing the pressure of the compressed air down to a pressure slightly higher than atmospheric pressure.

A demand valve 12 also allows air to be conveyed into the airtight mask 3 when the wearer inhales, and allows exhaled air to be discharged.

Various monitoring and alarm means 13 inform the wearer of how much air remains in the cylinder 6 and/or display information about the immediate surroundings.

Figure 2:
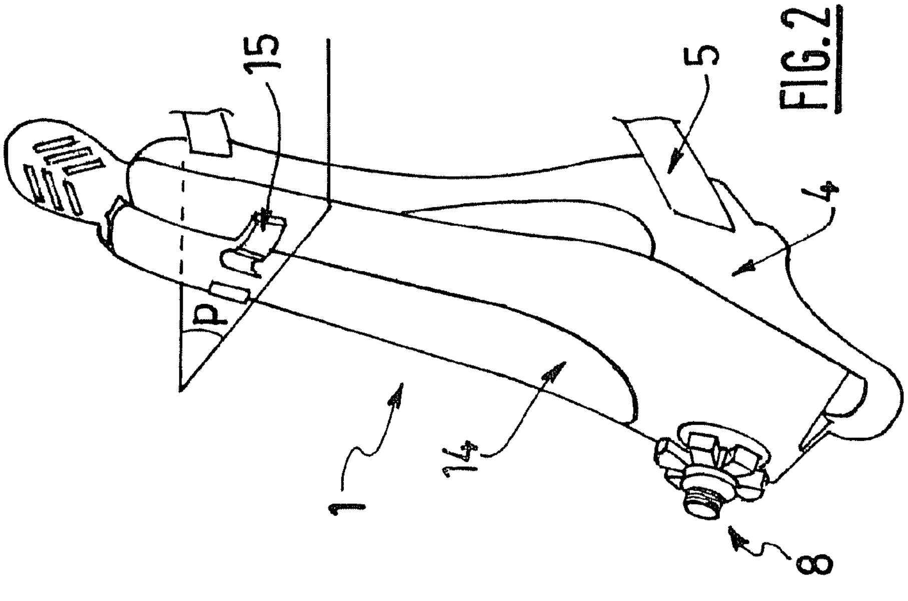

As can be seen more specifically in FIG. 2, the backpiece 4 equipped with the coupling 8 also comprises a cover 14 from which a cylinder support 15 projects. The cover 14 covers most of the backpiece 4 and has an opening 16 at the bottom through which the coupling 8, connected to the regulator (not visible), passes, so that it is protected by the cover.

Figure 3:
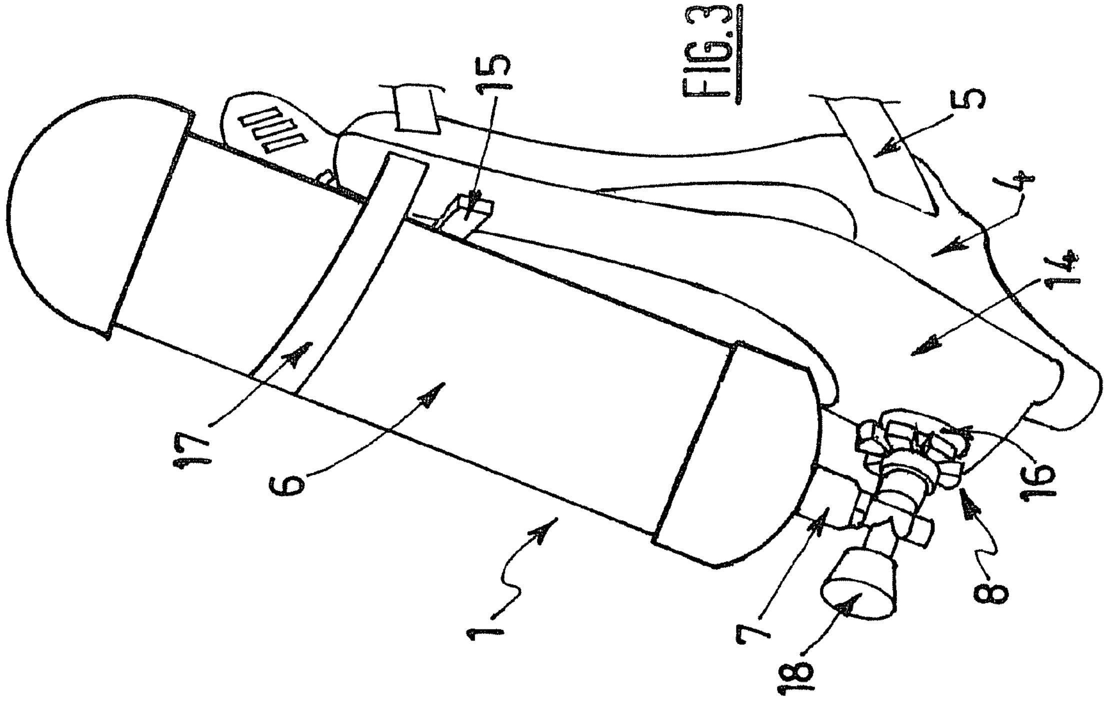
FIGS. 2 and 3 are perspective views of this apparatus, not equipped with a cylinder and equipped with a cylinder, respectively.

FIG. 3 shows the breathing apparatus 1 equipped with a cylinder 6 fixed to the backpiece 4 by means of a ratchet strap 17, as known per se, and resting on the support.

The valve of the cylinder 7 makes the connection between the neck of the cylinder 6 and the coupling 8, via a valve mechanism 18.

FIGS. 4 to 7 depict in detail the regulator 9 equipped with the coupling 8. The latter comprises an air intake tube 19, protruding outward, on which a bushing 20 is mounted such that it can pivot and move in terms of axial translation.

The bushing 20 comprises an externally threaded first region 21, situated toward the free end of the tube 19 and intended to collaborate with the tapped housing 22 of the valve 7 of the cylinder 6, as described hereinafter. The bushing 20 also comprises a second region 23 intended to be mounted in a sleeve 24 that forms an operating knob.

The screw-forming bushing 20 is prevented from turning in the sleeve 24 and is free in translational movement with respect to this sleeve.

This rotational coupling is achieved by means of screws 25 fixed into the second region 23 of the bushing 20, the screw heads being guided in translational movement by an oblong slot 26 formed in the sleeve 24, the axis of the slot being parallel to the axis of the tube.

The bushing 20 additionally comprises identification elements projecting into the oblong slot, secured to the second region 23 of the bushing 20.

The sleeve 24 is also mounted to pivot about the axis of the tube 19 and is prevented from performing any translational movement with respect to this tube.

The threaded region 21 of the bushing 20 and the sleeve 24 additionally define an annular space, of an outside diameter greater than the outside diameter of the valve 7, in its region 27 intended to collaborate with the coupling 8, and with an inside diameter substantially equal to the diameter of the housing 22 of the valve 7.

A helical compression spring 28 is positioned between the sleeve 24 and the bushing 20 so as to force the bushing 20 against a shoulder 29 of the air intake tube 19, this shoulder being produced at the free end of this tube.

The outside diameter of the tube 19, at its end region delimited by the shoulder 29, corresponds substantially to the diameter of the tapped housing 22 of the valve 7, for reasons which are detailed hereinafter.

The length of the sleeve 24 is greater than that of the bushing 20 and the length of the tube 19 is greater than the length of the bushing 20, increased by the depth of the housing 22 of the valve 7.

Figure 6:
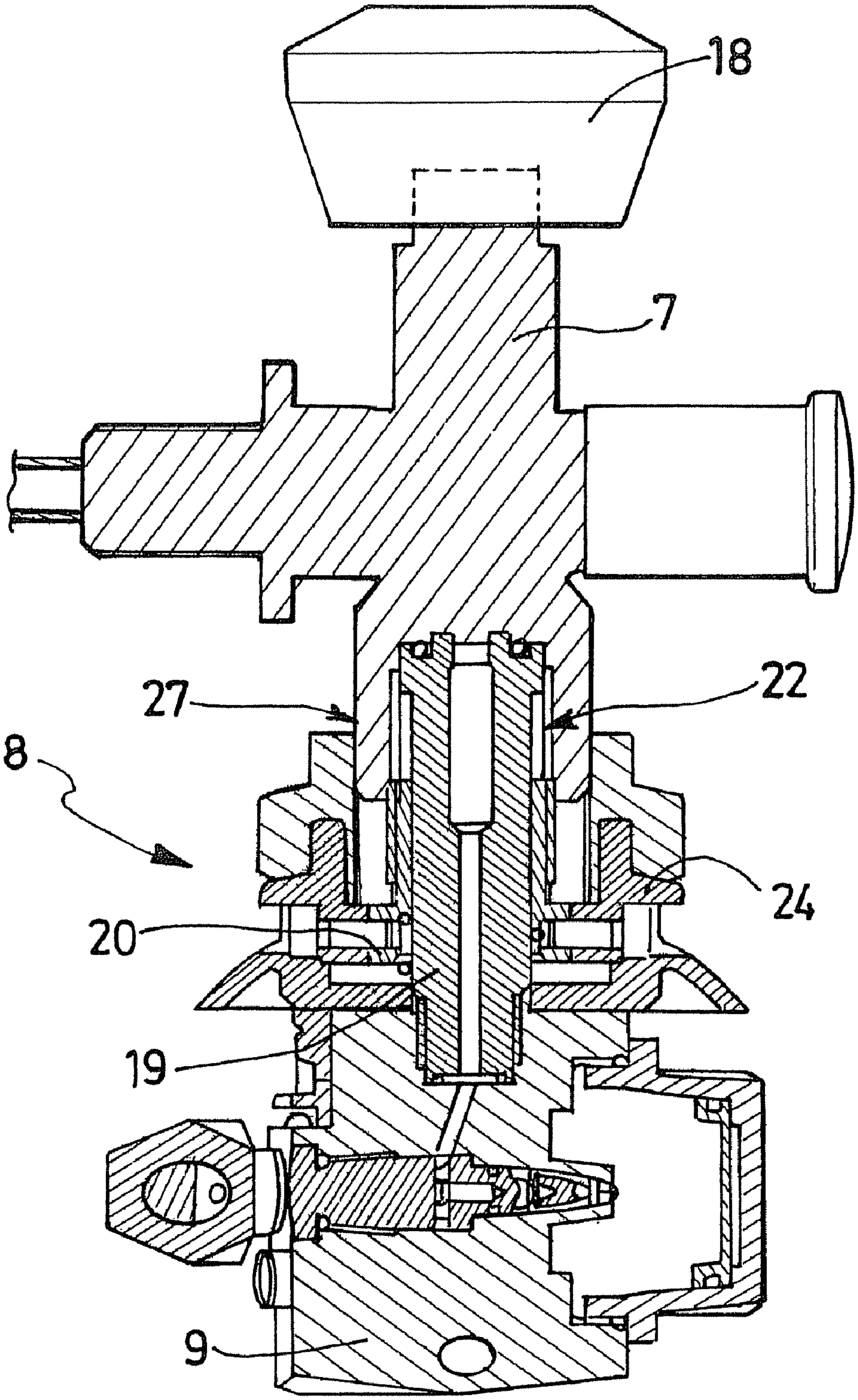
FIGS. 6 and 7 are views corresponding to FIG. 5, in which a valve of a cylinder is in the pushed-on position and in the position in which it is screwed on to the coupling, respectively.

When the valve 7 is being positioned on the coupling 8, as depicted in FIG. 6, the internal housing 22 of the valve 7 collaborates with the air intake tube 19 until the end of this tube comes into abutment against the end of the housing 22.

Because the end of the tube 19 is of a diameter substantially equal to that of the housing 22, the valve is therefore positioned correctly along the axis of the tube 19, and thus also along the axis of the bushing 20.

As the valve 7 is inserted, the bushing 20 is pushed back toward the regulator 9, against the force of the spring 28.

In this condition, the bushing 20 is completely situated inside the sleeve 24 and its threaded region 21 is forced against the tapped thread 22 of the valve.

By turning the sleeve 24, the bushing 20 is therefore screwed on to the valve 7. During screwing, the bushing 20 which is mounted such that it can move in terms of translation along the air intake tube 19, effects a translational movement toward the free end of this tube.

Figure 7:
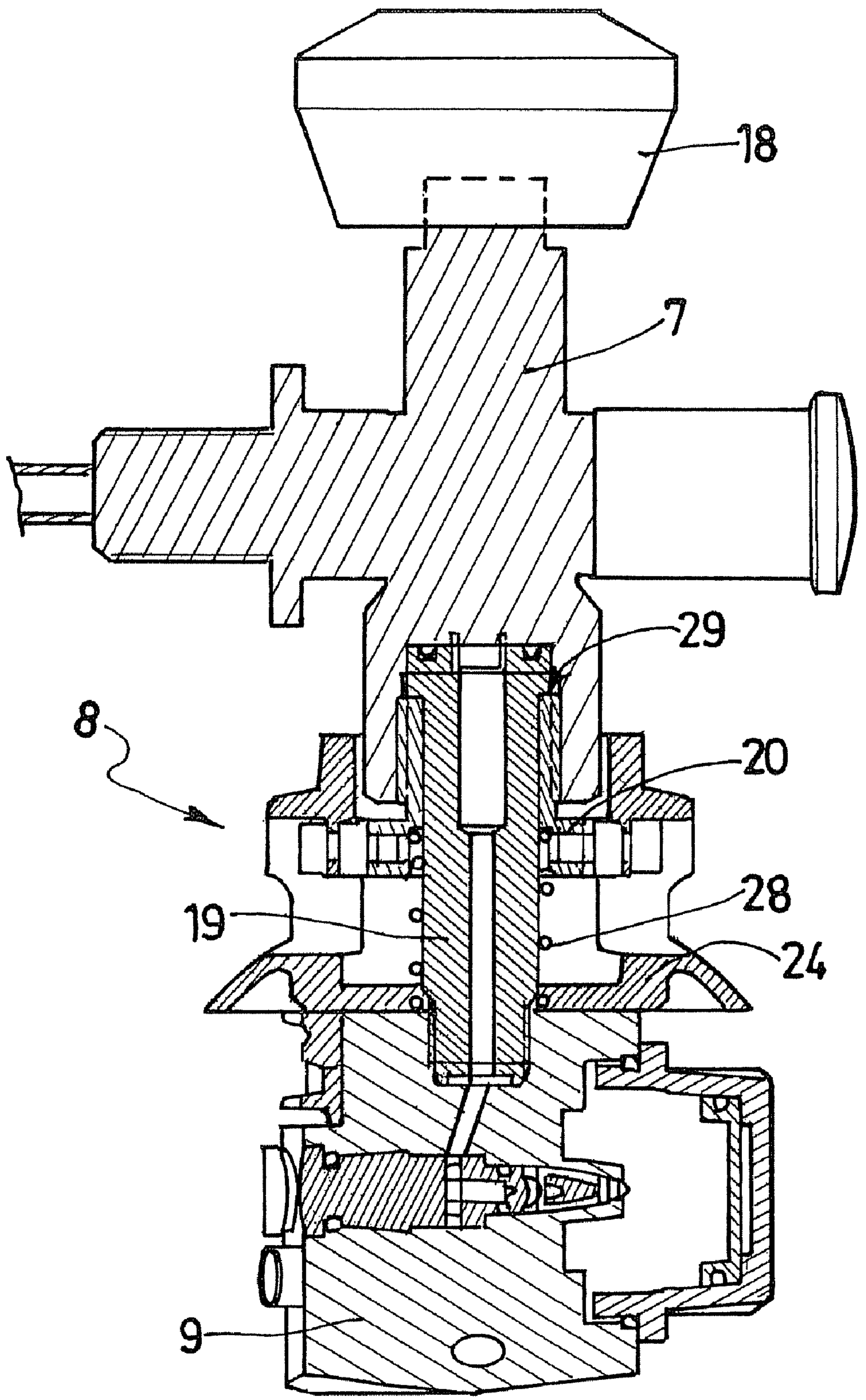

FIG. 7, which corresponds to FIG. 6, depicts the position of the bushing 20 at the end of screwing.

The identification elements 30 provide a better visual appreciation of the position of the bushing during screwing and/or unscrewing, so as to guarantee that the valve 7 is screwed correctly on to the coupling 8.

This coupling 8 makes it possible, in a first step, to be able to position the valve 7 correctly and easily on the tube 19, this tube forming a support, particularly when the cylinder 6 is exerting a force directed vertically downward on the valve 7, then allows the screwing step to be performed independently of the positioning.

The screwing operation is thus greatly facilitated, and the cylinder 6 can be changed quickly and easily even if the wearer is standing up.

Figure 8:
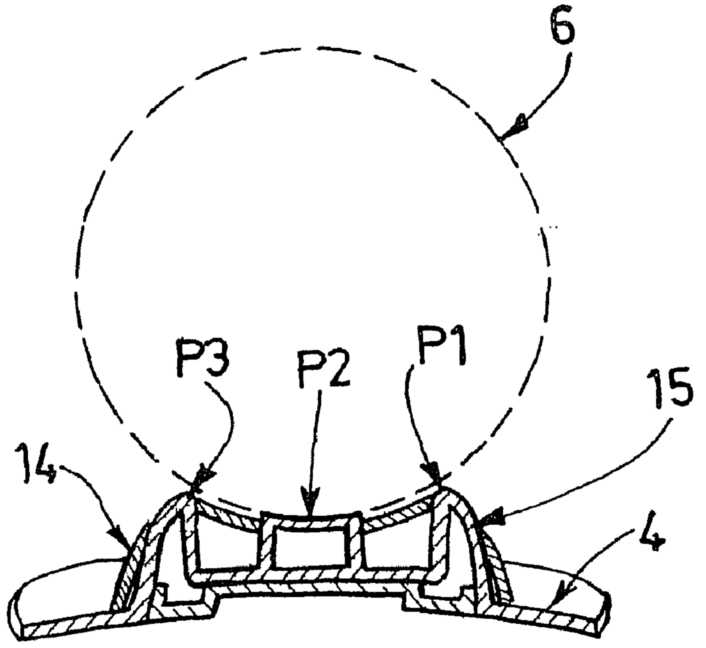
FIGS. 8 and 9 are views in section on the plane P, passing through the cylinder support, of respiratory apparatus equipped with one cylinder and with two cylinders, respectively.

According to one embodiment of the invention, the cylinder support 15 is molded into the backpiece 4 and projects outward with respect to the plane of the backpiece 4, as depicted in FIG. 8. The cover 14 also has openings through which the support 15 passes.

This support forms three points of contact P1 to P3, defining a V in a plane perpendicular to the plane of the backpiece 4, namely in the plane of section referenced P in FIG. 2. The cylinder 6, the external contours of which are depicted in dotted line, is fixed at its end to the coupling 8 via the valve 7 and rests on each of the three points P1 to P3 of the support 15. The cylinder 6 is held on the backpiece 4 by a strap that has not been depicted in this figure.

Figure 9:
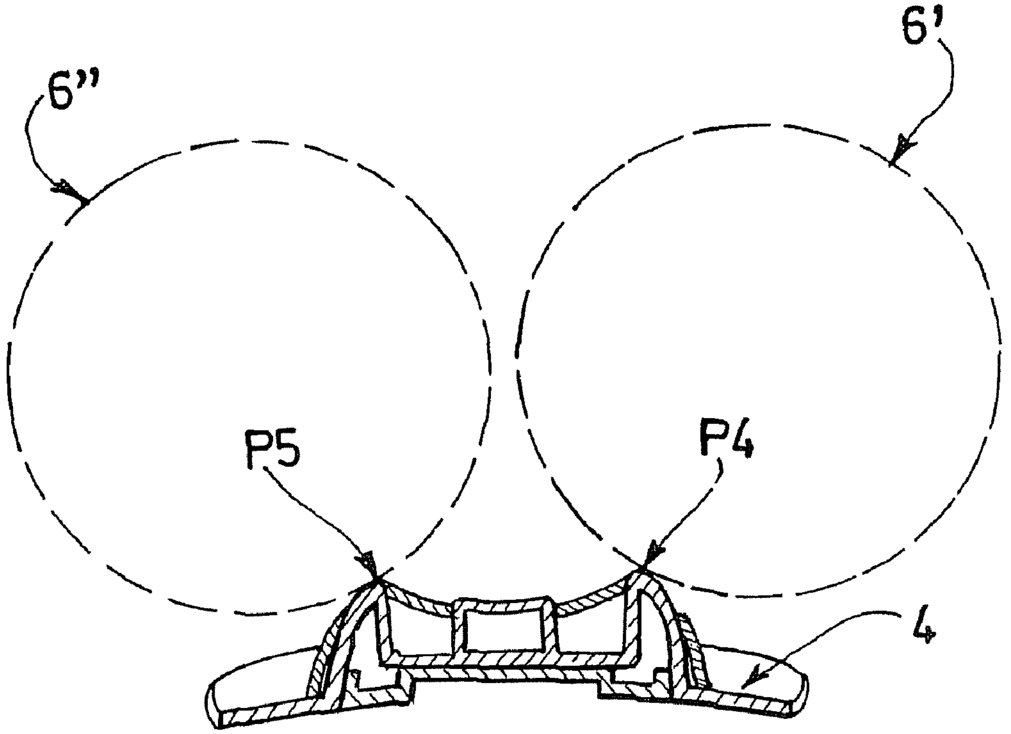

The support 15 also comprises two lateral points of contact P4 and P5 each able to support a cylinder 6', 6", as depicted in FIG. 9. As before, the two cylinders 6', 6" are fixed to the backpiece 4 by means of a strap that has not been depicted here.

It goes without saying, the invention is not restricted to the single embodiment of this system that has been described hereinabove by way of example, but encompasses all variants thereof.

The invention claimed is:

1. Breathing apparatus, particularly of the open-circuit type, comprising a backpiece equipped with means, particularly involving straps, to allow it to be worn on the back of a wearer, the backpiece being intended to support at least one cylinder equipped with a valve comprising a tapped internal housing, the backpiece being equipped with a coupling which, intended to collaborate with the valve, is connected to a regulator, wherein the coupling comprises an air intake tube, protruding outward, on which a bushing is mounted such that it can pivot and move in terms of axial translation, the bushing comprising an externally threaded first region situated toward the free end of the tube and intended to collaborate with the tapped housing of the valve of the cylinder, and a second region intended to be mounted in a sleeve that forms an operating knob, the screw-forming bushing being prevented from turning in the sleeve and free in terms of translational movement with respect to the latter, the sleeve being mounted such that it can pivot on the coupling about the axis of the tube and prevented from translational movement with respect to this tube.

2. The breathing apparatus as claimed in claim 1, wherein the free end of the tube comprises a region of a diameter substantially equal to a diameter of the housing of the valve.

3. The breathing apparatus as claimed in claim 1, wherein a length of the tube is at least equal to a depth of the housing increased by a length of the screw-forming bushing.

4. The breathing apparatus as claimed in claim 1, wherein an elastic element is mounted between the regulator or the sleeve and the bushing.

5. The breathing apparatus as claimed in claim 1, wherein a length of the sleeve is at least equal to a length of the bushing.

6. The breathing apparatus as claimed in claim 1, wherein the bushing is equipped with a coupling rod extending radially outward, the rod fitting into an oblong slot formed in the sleeve.

7. The breathing apparatus as claimed in claim 6, wherein the bushing is equipped with identification elements projecting into the oblong slot.

8. The breathing apparatus as claimed in claim 1 and which comprises a cover, fixed to the backpiece and at least partially covering the latter together with the regulator.

9. The breathing apparatus as claimed in claim 1 and which comprises a cylinder support having at least three points of contact positioned in such a way as to define a V directed at right angles to a plane of the backpiece, and which are intended to support a cylinder.

10. The breathing apparatus as claimed in claim 9, wherein the support comprises two additional lateral points of contact, each one intended to support a cylinder.

* * * * *